(12) United States Patent
Wellborn et al.

(10) Patent No.: US 7,918,784 B2
(45) Date of Patent: Apr. 5, 2011

(54) ENDOSCOPIC SURGICAL TOOL WITH RETRACTABLE BLADE FOR CARPAL TUNNEL RELEASE

(75) Inventors: Kenneth M. Wellborn, Charlottesville, VA (US); Clayton Peimer, Marquette, MI (US)

(73) Assignee: Microaire Surgical Instruments, Inc., Charlottesville, VA (US)

( * ) Notice: Subject to any disclaimer, the term of this patent is extended or adjusted under 35 U.S.C. 154(b) by 1149 days.

(21) Appl. No.: 11/470,439

(22) Filed: Sep. 6, 2006

(65) Prior Publication Data

US 2008/0045989 A1 Feb. 21, 2008

(51) Int. Cl.
*A61B 1/00* (2006.01)
*A61B 17/32* (2006.01)
(52) U.S. Cl. .................. 600/104; 600/149; 606/170
(58) Field of Classification Search .................. 600/104, 600/107; 606/170; 30/161
See application file for complete search history.

(56) References Cited

U.S. PATENT DOCUMENTS

| | | | | |
|---|---|---|---|---|
| 4,411,257 A | * | 10/1983 | Machida | 600/117 |
| 4,522,206 A | * | 6/1985 | Whipple et al. | 606/174 |
| 4,962,770 A | | 10/1990 | Agee | |
| 4,963,147 A | * | 10/1990 | Agee et al. | 606/170 |
| 5,089,000 A | | 2/1992 | Agee | |
| 5,306,284 A | * | 4/1994 | Agee et al. | 606/170 |
| 5,322,055 A | * | 6/1994 | Davison et al. | 601/2 |
| 5,562,600 A | * | 10/1996 | Matsuno | 600/107 |
| 5,569,160 A | * | 10/1996 | Sauer et al. | 600/114 |
| 5,735,865 A | * | 4/1998 | Schaumann et al. | 606/167 |
| 5,769,865 A | * | 6/1998 | Kermode et al. | 606/167 |
| 5,830,152 A | * | 11/1998 | Tao | 600/562 |
| 5,902,306 A | * | 5/1999 | Norman | 606/104 |
| 7,780,690 B2 | * | 8/2010 | Rehnke | 606/170 |
| 2003/0153938 A1 | * | 8/2003 | Masury et al. | 606/167 |
| 2006/0184187 A1 | * | 8/2006 | Surti | 606/170 |
| 2007/0123889 A1 | * | 5/2007 | Malandain et al. | 606/79 |
| 2007/0225740 A1 | * | 9/2007 | Suddaby | 606/170 |

* cited by examiner

*Primary Examiner* — Linda C Dvorak
*Assistant Examiner* — Alireza Nia
(74) *Attorney, Agent, or Firm* — Whitham Curtis Christofferson & Cook, PC

(57) ABSTRACT

An endoscopic tool utilizes a fiber optic system for illuminating and imaging ligaments or other tissue which are to be cut. Illumination and imaging is performed above a lateral opening at the distal end of a probe that is inserted into an incision point. Preferably, a two edged blade which can be moved in both the distal to proximal direction and the proximal to distal direction is selectively deployable from of the lateral opening at the distal end of the probe. The endoscopic tool is small in size, and preferably includes a pencil grip with a button actuator for deploying the two edged cutting blade. A wire actuator that fits into a slot in the bottom of the deployable blade, can be nested with the fiber optic cable such that the cross sectional area of the probe is reduced. Alternatively, a tube concentric with the fiber optic cable can be used as the mechanism for actuating the blade or other device. The surgeon can observe cutting of the ligament or other tissue as he moves the endoscopic tool in either or both the forward or reverse direction on a display screen which is operatively connected to the fiber optic system. A retractor can be used in conjunction with the endoscopic tool to lift tissue where dissection is desired, and to function as a guide for the blade.

11 Claims, 7 Drawing Sheets

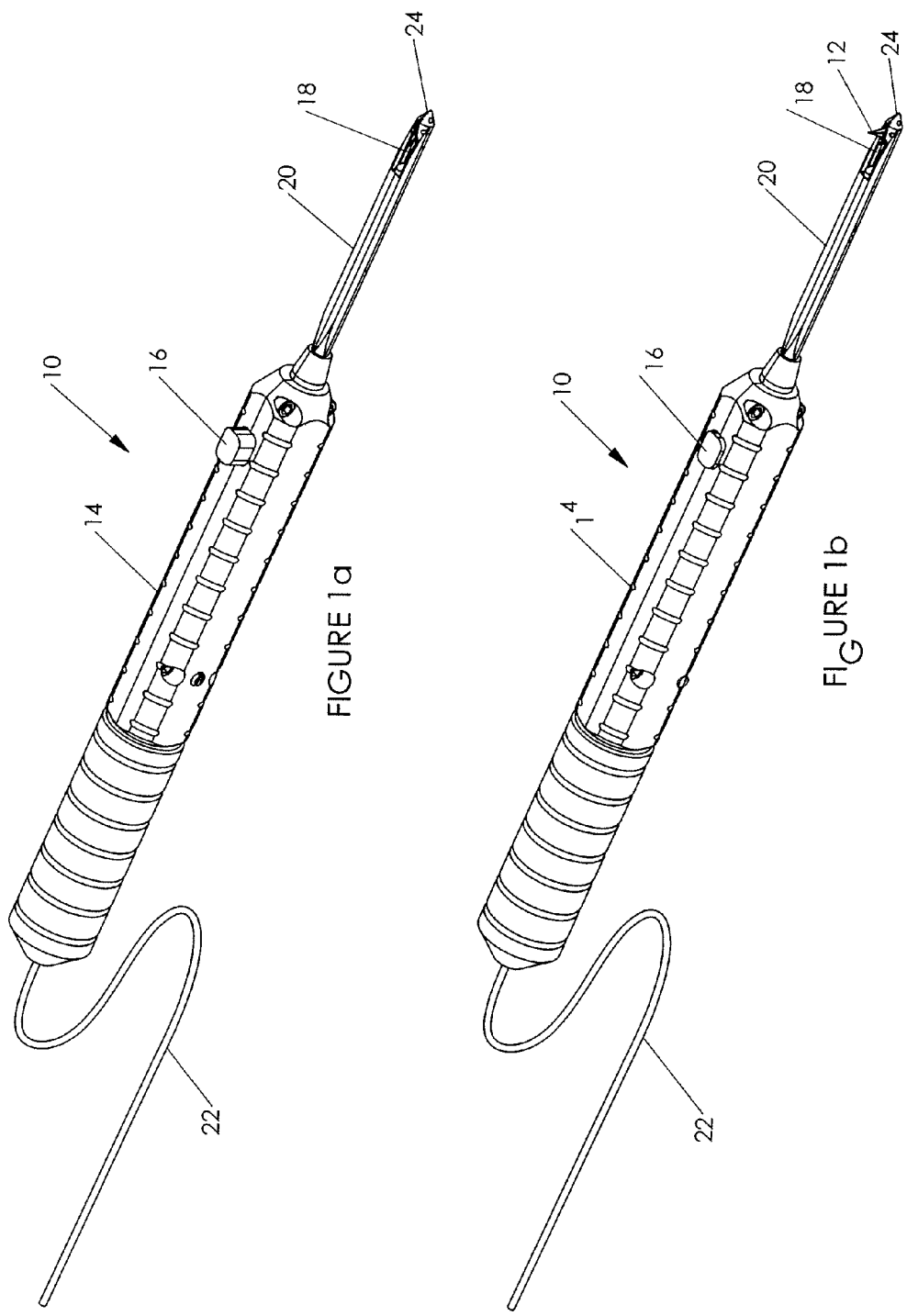

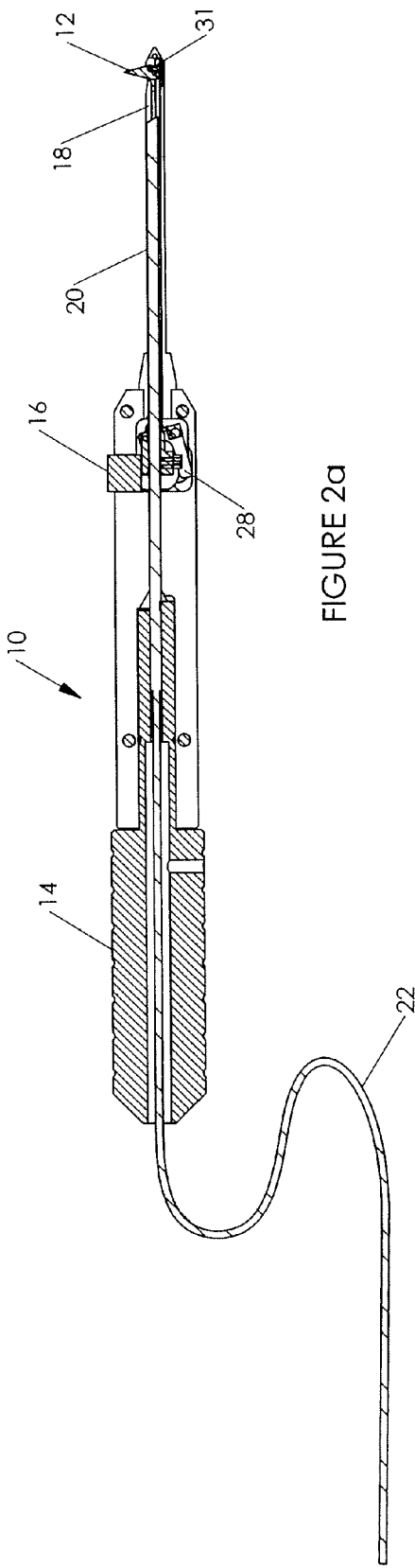
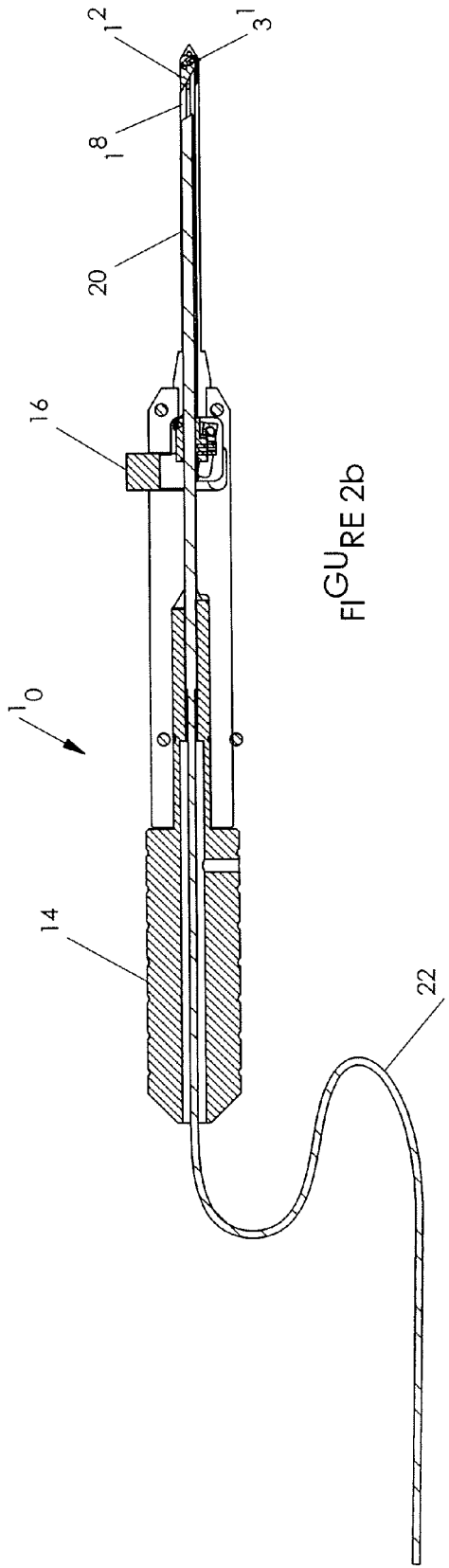
FIGURE 2a
FIGURE 2b

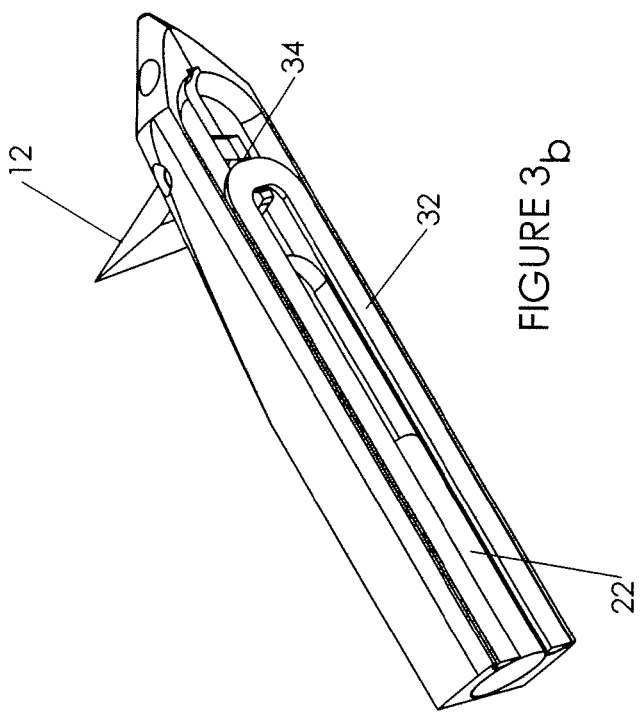
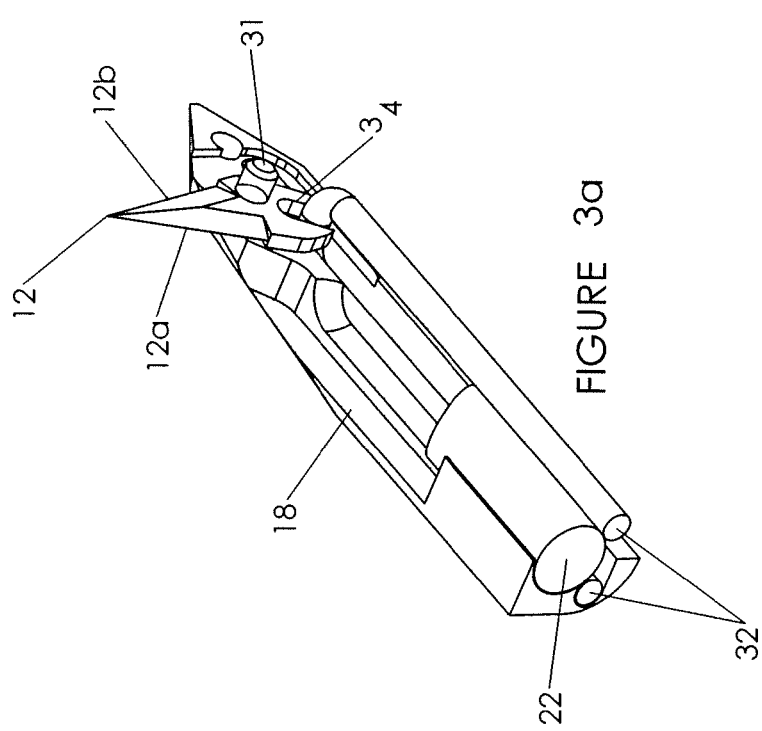
FIGURE 3a
FIGURE 3b

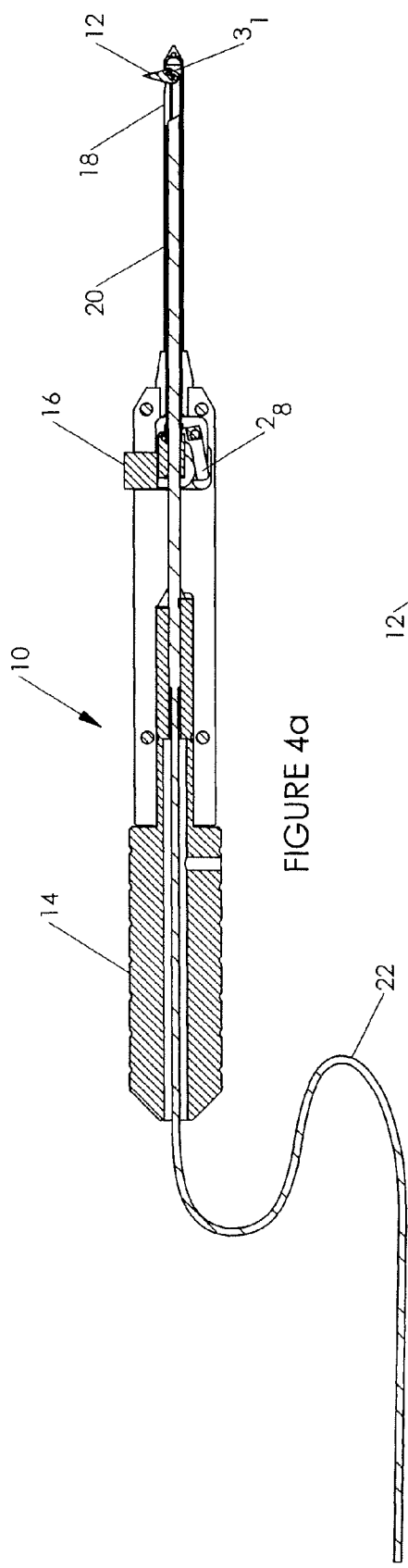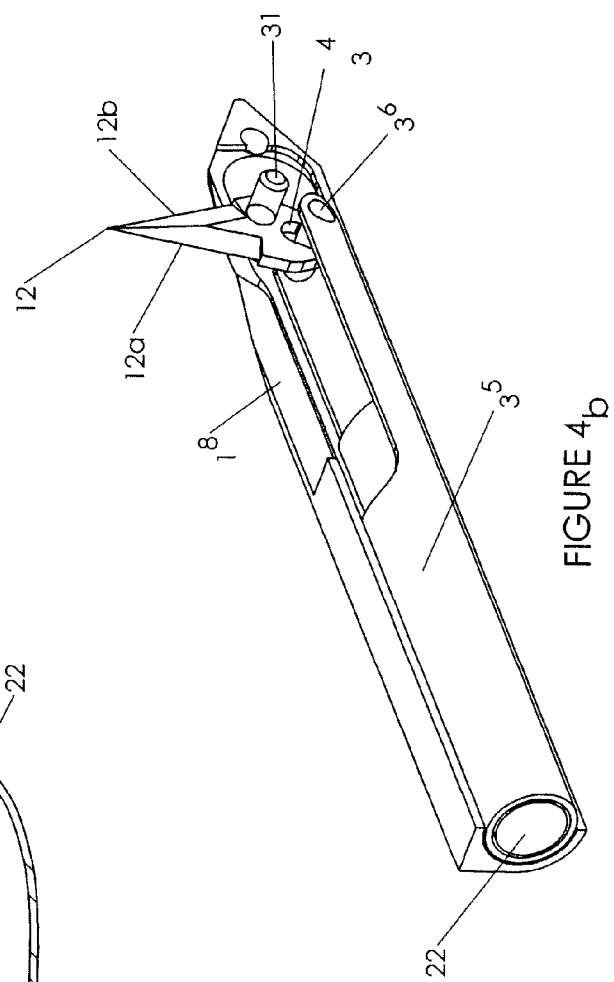
FIGURE 4a
FIGURE 4b

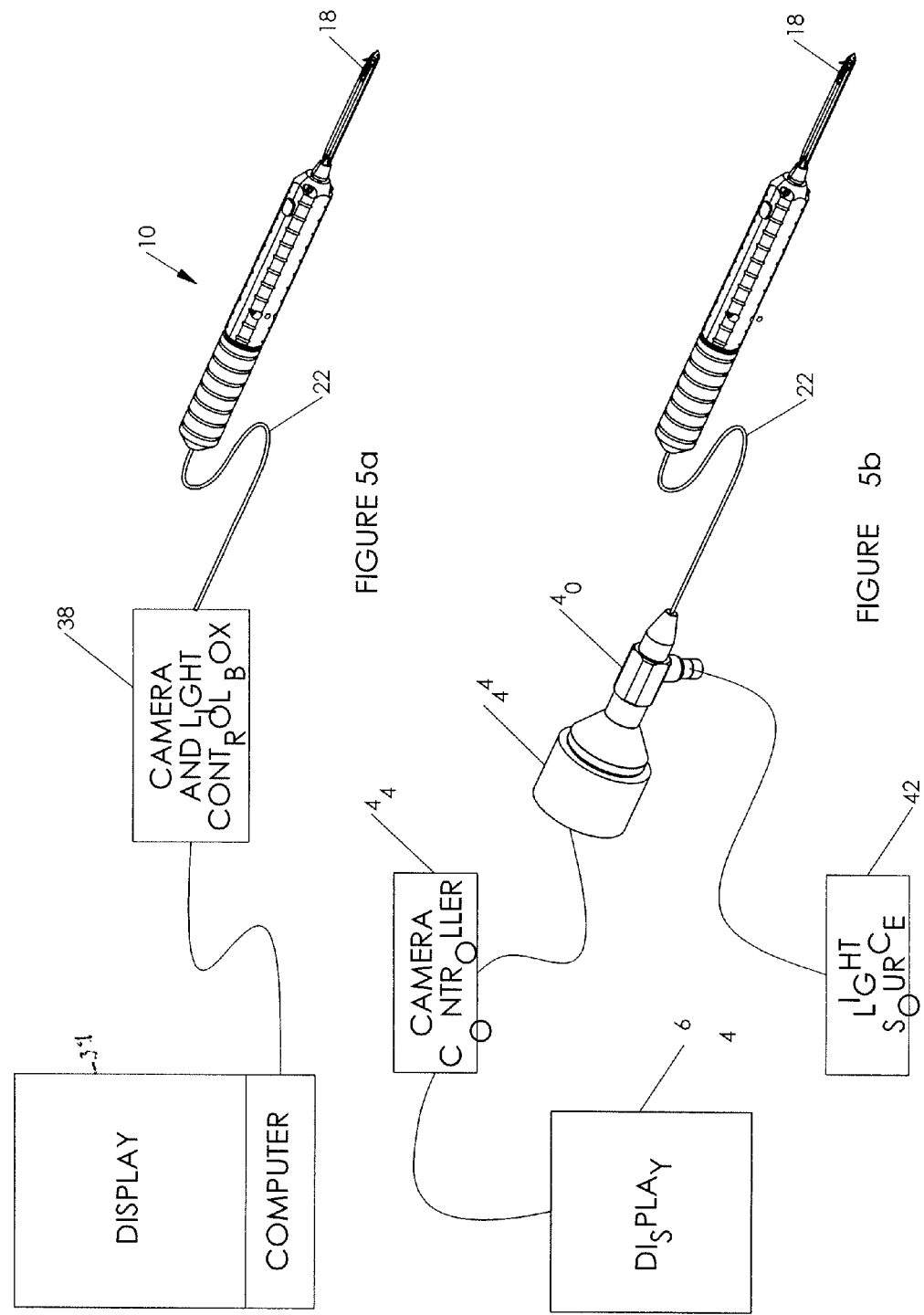

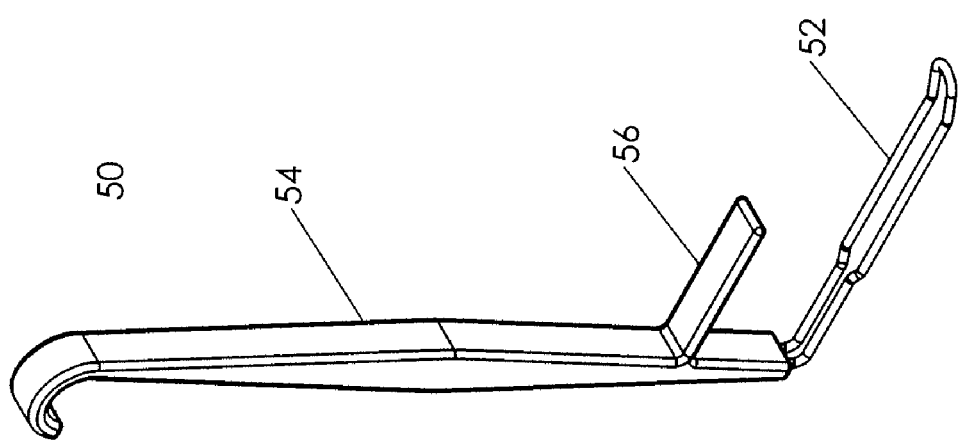

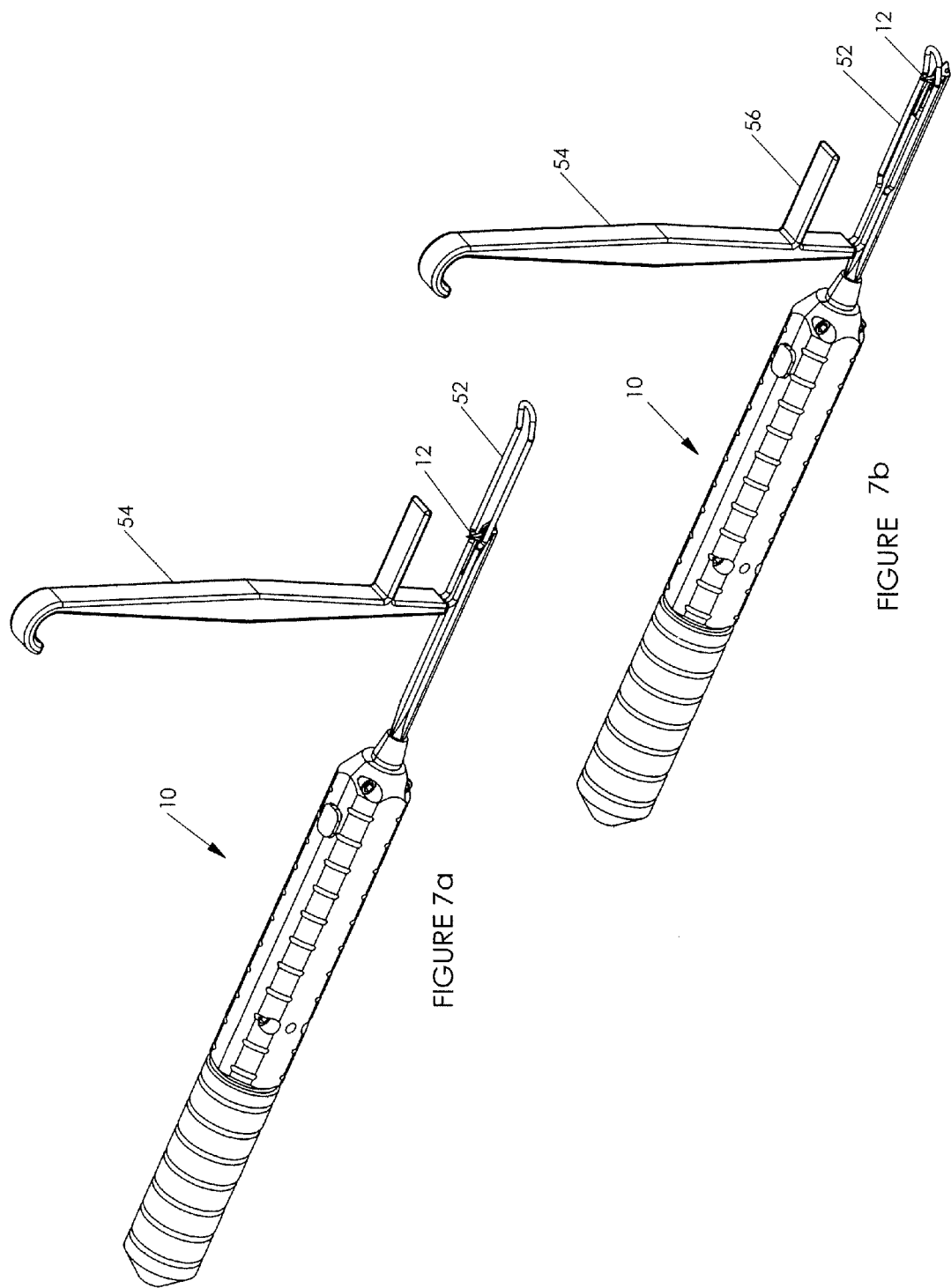

ENDOSCOPIC SURGICAL TOOL WITH RETRACTABLE BLADE FOR CARPAL TUNNEL RELEASE

BACKGROUND OF THE INVENTION

1. Field of the Invention

The present invention generally relates to endoscopic instruments, and is particularly related to surgical tools and procedures which can be used for the release of the transverse carpal ligament, as well as in other applications.

2. Background Description

Examples of surgical tools which are useful for inspecting and manipulating tissues (e.g., cutting of the transverse carpal ligament) in a body cavity are described in U.S. Pat. No. 4,962,770 to Agee, U.S. Pat. No. 4,963,147 to Agee, U.S. Pat. No. 5,089,000 to Agee, and U.S. Pat. No. 5,306,284 to Agee, each of which are herein incorporated by reference. The Agee patents show a probe which houses both a lens system and a selectively deployable blade. The lens system is used to illuminate and image tissue located above an opening in a top surface area of the probe near the probe's distal end. A pistol grip is provided which allows a surgeon to selectively deploy a blade out of the opening in the top surface once the probe is in the desired location. Preferably, the blade is deployed along a path that is close to perpendicular to the probe. The surgeon can then view the blade cutting the transverse carpal ligament for example, while the surgeon moves the probe backwards. This is done by observing the image on a display of the tissue located above the opening in the top surface of the probe. The Agee device allows dividing the flexor retinaculum, thereby releasing the carpal tunnel, while the optical system enables continuous observation of the cutting blade within the field of view above the opening in the probe.

The use of endoscopic instruments for the release of the transverse carpal ligament is a well-established surgical procedure. The devices consist of a cutting assembly for the dissection on the ligament and an endoscope with a camera system for visualization. All of the existing systems use a single edged blade for dissecting the ligament in either a distal to proximal motion or a proximal to distal motion. They also utilize rod lens endoscope technology that makes the instrumentation bulky and the endoscopes fragile. There is room for improvement both in performance and ease of use of the instrumentation to make the surgical procedure simpler and safer.

SUMMARY OF THE INVENTION

It is an object of this invention to provide a surgical instrument, which has particular application to carpal tunnel surgery but which can be used for imaging and cutting other tissues, which is of a small and conveniently handled size.

It is another object of this invention to provide a new method and surgical tool for cutting the carpal ligament.

It is yet another object of this invention to provide a more rugged and robust endoscopic tool.

It is still another object of this invention to provide a mechanism for selectively deploying devices such as cutting blades from an endoscopic tool that is small and compact, and which can fit neatly together with a fiber optic, but which does not significantly enlarge the diameter or volume of the probe end of the endoscopic tool.

An embodiment of the endoscopic surgical tool according to the invention preferably utilizes a retractable, double edged blade that is capable of dissecting the transverse carpal ligament in a distal to proximal motion as well as a proximal to distal motion. The instrument preferably uses a pencil style grip and is of a size which allows easier manipulation and operation than prior endoscopic devices. Dissection of the transverse carpal ligament by movement of the cutting tool in both a distal to proximal direction and a proximal to distal direction allows for greater flexibility in operation, as well as improved accuracy. The endoscopic surgical tool may be used for cutting and manipulating other tissues which are different from the transverse carpal ligament. In addition, devices other than double edged blades may be selectively extended from the probe tip.

In a preferred embodiment, a fiber optic bundle is used to supply light for illumination, and to allow for imaging of tissue localized near the probe tip. One benefit of using fiber optics is that it allows for the camera and light cable to be remote from the instrument, which makes the instrument more precise and less bulky. Using fiber optics in the endoscopes also make them much more durable because the shaft is flexible, unlike rod lens endoscopes.

The endoscope can use either a traditional c-mount camera and light cable for use with an endoscopic tower or a dedicated control box that includes a camera and light source that can be connected directly to a computer.

The endoscopic surgical tool preferably employs either a tubular actuator which fits over and is movable relative to the fiber optic or a wire actuator which can be nested with the fiber optic in the probe tip. The actuator mechanism is preferably as small as possible so that the diameter (and volume) of the probe tip is small, thereby allowing for easier manipulation of the tool and minimizing damage to neighboring tissue to the probe tip when the tool is used. The endoscopic tool of the present invention may, for example, have a diameter that is less than half the size of the commercial tools made according to the Agee patents noted herein which are offered by MicroAire Surgical Instruments. Furthermore, the actuator mechanism may advantageously be used on tools which are not specific for performing carpal tunnel surgery in that the mechanism permits, for example, cutting tools to be precisely deployed from or retracted into a housing inserted into the body, but do not adversely increase the volume of the housing.

In an embodiment of the instrumentation, a retractor is included which can be inserted into the incision with the instrument to support the ligament and surrounding tissue for better visualization while the ligament is dissected. The retractor preferably includes a "U" shaped wire that enables the instrument to cut inside the "U" while it is supporting the tissue. That is, the retractor can function as a guide for the instrument that allows the surgeon to dissect only the retracted tissue and protect the other anatomy (median nerve and tendons) that are in proximity to the retracted tissue. The retractor may have a sight that allows the surgeon to position the retractor in the correct location, which also helps the surgeon avoid cutting other anatomy during the dissection of the ligament.

Some of the advantages of the new instrumentation are:

Double edged blade that will dissect the transverse carpal ligament both in a distal to proximal motion and a proximal to distal motion Fiber optic endoscope that allows for the camera and light cable to be connected remotely which makes for a more precise instrument and offers better durability than a rod lens endoscope Retractor to provide better visualization during the dissection, guide the instrument as it dissects, and provide external sighting for correct location of the dissection.

BRIEF DESCRIPTION OF THE DRAWINGS

The foregoing and other objects, aspects and advantages will be better understood from the following detailed description of a preferred embodiment of the invention with reference to the drawings, in which:

FIGS. 1a and 1b show isometric views of the a preferred embodiment of the endoscopic tool according to this invention;

FIGS. 2a and 2b are cut away cross-sectional views of an endoscopic tool with the two edged blade deployed and retracted, respectively;

FIGS. 3a and 3b show an exemplary embodiment of a blade deploying mechanism which can be used with the endoscopic tool;

FIGS. 4a-b show a second exemplary embodiment of a blade deploying mechanism which can be used with the endoscopic tool;

FIGS. 5a and 5b are schematic views of different embodiments of the endoscopic instrumentation of this invention where the fiber optic cable is respectively connected to a dedicated control box that includes a camera and light source which may be connected directly to a computer, or connected to a more traditional endoscopic tower;

FIG. 6 is an isometric view of a retractor device;

FIGS. 7a and 7b show the endoscopic tool and retractor device being used together, whereby the retractor functions as a lifting element and cutting guide, and the dual edge cutting blade of the endoscopic tool cuts when the tool is moved in the distal to proximal (e.g., 7b to 7a) or the proximal to distal (e.g., 7a to 7b) directions.

DETAILED DESCRIPTION OF THE PREFERRED EMBODIMENTS OF THE INVENTION

Referring now to the drawings, and more particularly to FIGS. 1a and 1b, there is shown a pencil grip style endoscopic tool 10. The tool 10 has features which are similar to parts of the endoscopic tools described in U.S. Pat. No. 4,962,770, U.S. Pat. No. 4,963,147, U.S. Pat. No. 5,089,000 and U.S. Pat. No. 5,306,284 to Agee, each of which are herein incorporated by reference; however, the tool 10 is generally smaller in size, uses different lighting and imaging technologies, and has a blade 12 which cuts in two directions. The tool 10 has a handle 14, with a button actuator 16. As can be seen from a comparison of FIG. 1a and FIG. 1b, when the actuator 16 is depressed by the surgeon using his or her thumb or by other means towards the handle 14, the blade 12 is deployed from the lateral opening 18 located near the end of the probe 20.

A fiber optic cable 22 extends through the handle 14, to the opening 18 near the end of the probe 20. The fiber optic cable 22 allows light to be transmitted out the opening 18 for illuminating tissue positioned above the opening 18, and allows the area above the opening 18 to be imaged and displayed at a remote location. Thus, after the probe 20 is inserted into an incision, the surgeon will move the probe to the location he or she deems suitable for performing a cutting/dissection function. A rounded or pointed end 24 of the probe 20 helps separate tissues as the surgeon moves the probe 20 into position. As will be discussed below in connection with FIGS. 3a-b and 4a-b, the tool 10 preferably includes a compact actuator mechanism that is nested with or which slides over the fiber optic cable 22, so that the diameter of the probe is small which allows the probe to be moved after insertion through the incision in the patient's tissue with more ease than previous tools which use lens systems. The surgeon can view the image of tissues, ligaments, etc. above the opening of the probe 20 on a screen. Once the probe 20 is located where cutting is desired, the blade 12 can be deployed out of the opening. The blade 12 is preferably sharpened on both sides to allow cutting with movement in both the forward (proximal to distal) and rearward (distal to proximal) directions. The blade 12 is sharpened to a point to allow the penetrating of the ligament in the middle and cutting in either direction. The blade 12, and its relationship to the ligament above opening 18, are viewed on a screen due to the image being transmitted by the fiber optic cable 22, so that the surgeon can see the blade cutting the ligament on a screen as he or she moves the probe in the forward or reverse direction.

FIGS. 2a and 2b show an embodiment of the endoscopic tool 10 whereby the blade 12 is show to pivot from an orientation with the tip facing proximally, to an orientation with the tip perpendicular to the probe 20 upon depression of the button 16. Depressing button 16 pivots lever 28 (FIG. 2), allowing a spring biased actuator to move proximally, which causes the blade 12 to pivot about point 31 so as to deploy the blade out of the lateral opening 18. However, it should be recognized that a wide variety of other mechanisms may be used for allowing the blade to be deployed.

FIGS. 3a-b show an exemplary embodiment of the blade actuating mechanism. A wire 32 shaped in the form of a "U" is nested with the fiber optic cable 22 inside the probe and is attached to lever 28. The wire 32 engages the blade 12 in slot 34 which allows the wire 32 to raise and lower the blade 12. This saves considerable space and allows the cross-sectional area of the probe to be considerably smaller than the tools modeled on U.S. Pat. No. 4,962,770, U.S. Pat. No. 4,963,147, U.S. Pat. No. 5,089,000 and U.S. Pat. No. 5,306,284 to Agee. As best shown in FIGS. 3a and 3b the wire 32 fits in slot 34 at the base of blade 12. As the wire 32 moves proximally upon depression of the button 16 on the handle 14, the blade 12 pivots about pin 31 and is deployed out the lateral opening 18. The end of the fiber optic cable 22 allows the ligament above the probe to be viewed, as well as the blade 12, such that the surgeon can observe cutting of the ligament with movements both in the distal to proximal direction (cutting with side 12a in FIG. 3a) and in the proximal to distal direction (cutting with side 12b in FIG. 3a).

FIGS. 4a-b show an alternate embodiment of the blade actuating mechanism. A cylindrical tube 35 is used concentric to the fiber optic cable 22 inside the probe 20 and is attached to lever 28. FIG. 4b shows that the tube 35 has a pin 36 attached that engages the blade 12 in slot 34. The inner diameter is such that it permits movement of the tube 35 relative to the fiber optic cable, but will be generally close in dimension to the outer diameter of the fiber optic cable. The tube can be made of a wide variety of materials including polymer, metals or composites. The blade 12 is deployable and retractable by pivoting on pin 31. The tube 35 has a partial opening which extends past the end of the fiber optic cable 22 which allows the blade to be held within the probe housing when it is retracted.

Both the blade opening mechanism shown in FIGS. 3a-b and the blade opening mechanism shown in FIG. 4a-b have the advantage that they contribute very little to the cross-sectional area of the probe tip. In FIG. 3a-b, the nested arrangement of the wire 32 only increases the diameters of the probe tip by an amount equal to the thickness of the wire. While in FIG. 4a-b, the cross sectional area of the probe tip is increased by an amount approximately the same size as the thickness of the tubing 35. Other actuator mechanisms might be used in the practice of the invention shown in FIGS. 1a-b. Furthermore, the blade opening mechanism might be used advantageously in other surgical tools (e.g., tools not used for carpal tunnel surgery) and to deploy other devices (e.g., pins, hooks, viewing devices, single sided blades, etc.). In addition, while FIGS. 3a-b and 4a-b show a slot 34 as the engagement mechanism on the base of the blade, and either a wire 32 or pin 36 as the engagement mechanism that is actuated when the button 16 is depressed, it should be understood that other mechanisms might also be employed (e.g., a pin fused to the blade, which is captured by slots in tube 35, etc.).

FIG. 5a shows the fiber optic cable 22 from the endoscopic surgical tool 10 being directed to a camera and light control box 38. This box 38 does not need to be physically supported by the surgeon during operation of the endoscopic tool. The camera and light control box 38 allows the surgeon to selectively turn on and off the camera for imaging and to turn on and off, and, in some applications adjust, the lighting which is directed out of the opening 18. The feed from the camera and light control box 38 can be sent to a computer with a display 39. The display 39 will preferably be positioned so that the surgeon can observe cutting operations during surgery. In addition, the images taken during surgery can be stored to a hard drive or other storage medium FIG. 5b shows an alternative and more traditional endoscopic tower configuration. Here the fiber optic cable is 22 is directed from the endoscopic tool to a joint 40 which has one section directed to a light source 42 and another section directed to a camera 44. A camera controller 46 controls operations of the camera 44 and sends a feed to display 46 which can be observed by the surgeon during surgery. The fiber optic cable carries both light and images, and the joint 40, essentially divides the light carrying fibers from the bundle. The light source 42 can be turned on and off, and in some applications the intensity of the light can be adjusted. As discussed above, the light is projected out of the opening 18 at the distal end of the probe 20. Images obtained at the opening are then viewable on the display 46.

FIG. 6 shows a retractor 50 which can be used in conjunction with the endoscopic tool 10. The retractor 50 preferably has a wire projection 52 which is inserted into an incision in the patient's skin. The wire projection 50 is stiff such that the surgeon can use the handle 54 as a lever so that the wire projection 52 can lift tissues under the skin. A sight 56, which for example, can be a simple projection that is oriented in the same direction as the wire projection 52, can be positioned on the handle 54 to aid the surgeon in properly aligning the retractor. The sight 56 would be above the patient's skin and would reflect the orientation of the wire projection 52 below the patient's skin.

FIGS. 7a and 7b show that the wire projection 52 can preferably function as a guide for the blade 12 after it is deployed from the endoscopic tool 10. In this way, the wire projection 52 lifts and protects nerves and other tissues so that on the ligament (or other tissue) is cut by the surgeon when performing an operation. The wire projection 52 may also improve the imaging that can be made above the opening 18 with the endoscopic tool by lifting the tissue and spreading it over the opening 18. The blade 12 can be moved forward and backward inside the wire projection 62, cutting in both directions. The ability to cut in both directions allows for a more robust endoscopic tool than has been used previously.

While the invention has been described in terms of its preferred embodiments, those skilled in the art will recognize that the invention can be practiced with modification within the spirit and scope of the appended claims.

I claim:

1. An endoscopic carpal tunnel release tool, comprising:
   a hand grip in the form of a pencil grip; a probe extending from the hand grip in line with said hand grip, said probe having an opening formed in an upper on-a-side surface towards a closed distal end;
   a blade positioned in said opening of said probe which is selectively deployable from said opening;
   a fiber optic extending through said hand grip and said probe for supplying light to said opening and for permitting imaging at said opening of said probe; and
   an actuator positioned on said hand grip, wherein said actuator includes a U shaped wire nested with said fiber optic which fits in a slot at a base of said blade, wherein said actuator on said hand grip is mechanically connected to said U shaped wire and said blade for selectively deploying said blade from said opening, said actuator positioned on said hand grip being aligned with said opening formed in said upper side surface of said probe.

2. The endoscopic carpal tunnel release tool of claim 1 wherein said actuator includes a depressible button.

3. The endoscopic carpal tunnel release tool of claim 1 wherein said blade includes two cutting edges and is pivotable from a direction where a tip is oriented toward said hand grip to a position where said tip is approximately perpendicular to said probe.

4. The endoscopic carpal tunnel release tool of claim 1 wherein said actuator includes a tube concentric with said fiber optic which includes a pin which fits in a slot at a base of said blade.

5. The endoscopic carpal tunnel release tool of claim 1 further comprising a display for receiving images obtained using said fiber optic.

6. The endoscopic carpal tunnel release tool of claim 1 wherein said blade includes a slot.

7. An endoscopic surgical tool, comprising:
   a hand grip in the form of a pencil grip;
   a probe extending from the hand grip in line with said hand grip, said probe having an opening formed in an upper side surface towards a closed distal end;
   an optical fiber positioned within said probe for
      (i) providing illumination from said opening in said probe
   and/or
      (ii) allowing imaging of tissue at said opening;
   a movable sleeve concentric with said optical fiber and positioned within said probe and movable in a longitudinal direction within said probe, said movable sleeve having an extension portion which includes two side members on opposite sides of said optical fiber where each of said two side members extends beyond an end of said optical fiber, wherein said end of said optical fiber is aligned with said opening in said probe;
   a cutting blade which is pivotably connected to said probe by a first pin, and which is connected to said two side members of said extension portion of said movable sleeve by a second pin;
   wherein longitudinal movement of said movable sleeve causes pivoting of said cutting blade about said first pin due to longitudinal movement of said second pin whereby an extendible portion of said cutting blade is either selectively extended from said opening of said probe; and
   an actuator positioned on said hand grip mechanically connected to said movable sleeve and said cutting blade for selectively deploying said blade from said opening, said actuator positioned on said hand grip being aligned with said opening formed in said upper side surface of said probe.

8. The endoscopic surgical tool of claim 7 wherein the cutting blade has cutting surfaces on its forward and reverse edges.

9. The endoscopic surgical tool of claim 7 where the optical fiber is present with a plurality of fibers in a fiber bundle.

10. The endoscopic surgical tool of claim 7 wherein said engagement members comprise a pin connected to said extension portion of said movable sleeve, and a slot in a base of said device.

11. An endoscopic surgical tool, comprising:
   a hand grip in the form of a pencil grip;
   a probe extending from the hand grip in line with said hand grip, said probe having an opening formed in an upper side surface towards a closed distal end
   an optical fiber positioned within said probe for
      (i) providing illumination from said opening in said probe,
   and/or
      (ii) allowing imaging of tissue at said opening;
   a U shaped wire nested with said optical fiber, said U shaped wire extends beyond an end of said optical fiber;
   a device which is pivotably connected to said probe; and
   an engagement member on said device which engages said U shaped wire, wherein movement of said U shaped wire causes pivoting of said device whereby an extendible portion of said device is either selectively extended from said opening of said probe or positioned within said opening in said probe, and
   an actuator positioned on said hand grip mechanically connected to said U shaped wire and said device for selectively extending said device from said opening or positioning said device within said opening, said actuator positioned on saint hand grip being aligned with said opening formed in said upper side surface of said probe.

* * * * *

UNITED STATES PATENT AND TRADEMARK OFFICE
CERTIFICATE OF CORRECTION

PATENT NO.           : 7,918,784 B2                      Page 1 of 1
APPLICATION NO.      : 11/470439
DATED                : April 5, 2011
INVENTOR(S)          : Kenneth M. Welborn et al.

It is certified that error appears in the above-identified patent and that said Letters Patent is hereby corrected as shown below:

On the Title Page, first Item 75 Inventor name to read as follows:

Kenneth M. Welborn

Signed and Sealed this
Tenth Day of May, 2011

David J. Kappos
*Director of the United States Patent and Trademark Office*